US009863862B2

(12) United States Patent
Han

(10) Patent No.: US 9,863,862 B2
(45) Date of Patent: Jan. 9, 2018

(54) METHOD AND SYSTEM FOR SIGNIFICANTLY IMPROVING CHARGE PROBABILITIES OF NANOMETER AEROSOL PARTICLES

(71) Applicant: TSI Incorporated, Shoreview, MN (US)

(72) Inventor: Hee-Siew Han, Maple Grove, MN (US)

(73) Assignee: TSI INCORPORATED, Shoreview, MN (US)

( * ) Notice: Subject to any disclaimer, the term of this patent is extended or adjusted under 35 U.S.C. 154(b) by 272 days.

(21) Appl. No.: 14/209,179

(22) Filed: Mar. 13, 2014

(65) Prior Publication Data

US 2014/0268476 A1 Sep. 18, 2014

Related U.S. Application Data

(60) Provisional application No. 61/786,993, filed on Mar. 15, 2013.

(51) Int. Cl.

*G01N 15/06* (2006.01)
*G01N 15/02* (2006.01)
*B05B 5/03* (2006.01)
*G01N 15/00* (2006.01)

(52) U.S. Cl.

CPC ..... *G01N 15/0656* (2013.01); *G01N 15/0266* (2013.01); *B05B 5/032* (2013.01); *G01N 2015/0046* (2013.01)

(58) Field of Classification Search

CPC . B05B 5/032; G01N 15/0266; G01N 15/0656
USPC .................................................. 361/226–228
See application file for complete search history.

(56) References Cited

U.S. PATENT DOCUMENTS 6,712,881 B2 3/2004 Hering et al.
6,965,240 B1 * 11/2005 Litton ................ G01N 15/0656 324/448
7,407,531 B2 8/2008 Flagan et al.
7,796,727 B1 * 9/2010 Kaufman .................. H05F 3/06 378/64

(Continued)

OTHER PUBLICATIONS

Iida, Kenjiro, et al. "Effect of Working Fluid on Sub-2nm Particle Detection with a Laminar Flow Ultrafine Condensation Particle Counter," Aerosol Science and Technology, 43:81-96, 2009 (17 pages).

(Continued)

*Primary Examiner* — Thienvu Tran
*Assistant Examiner* — Christopher Clark
(74) *Attorney, Agent, or Firm* — Kagan Binder, PLLC

(57) ABSTRACT

The various embodiments described herein significantly increase charge probabilities of nanoparticles by first growing them to larger droplets using a diethylene glycol-based preconditioner, neutralizing the droplets with a bipolar charger, and then removing the condensed liquid to recover the original aerosol particles. The small droplet size is an important element in reducing the amount of aerosol particles with more than one charge. The high single-charge particle probability significantly enhances the monodisperse aerosol throughput of a DMA, while the reduced multiple charge probabilities ensure high monodispersity of DMA-classified aerosols and good data quality of SMPS measurements.

16 Claims, 2 Drawing Sheets

(56) References Cited

U.S. PATENT DOCUMENTS

| | | | | |
|---|---|---|---|---|
| 8,047,055 | B2 * | 11/2011 | Wang | G01N 15/0205 250/287 |
| 9,212,983 | B2 * | 12/2015 | Tsunoda | G01N 15/0266 |
| 2005/0183518 | A1 * | 8/2005 | Neuefeind | G01N 23/20 73/863.11 |
| 2006/0284077 | A1 * | 12/2006 | Fissan | G01N 23/00 250/288 |
| 2008/0302666 | A1 * | 12/2008 | Benner | G01N 15/0266 204/645 |
| 2009/0183554 | A1 * | 7/2009 | Grant | G01N 1/4022 73/61.71 |
| 2010/0031734 | A1 * | 2/2010 | Zhang | G01N 33/18 73/61.43 |
| 2011/0246089 | A1 * | 10/2011 | Barrett | G01N 15/0266 702/24 |
| 2012/0048112 | A1 * | 3/2012 | Hering | B01D 5/0009 95/228 |
| 2012/0131989 | A1 * | 5/2012 | Vanhanen | G01N 15/06 73/28.01 |
| 2013/0265574 | A1 * | 10/2013 | Buckley | G01N 15/0618 356/313 |
| 2013/0321804 | A1 * | 12/2013 | Kulkarni | G01J 3/443 356/316 |
| 2014/0029154 | A1 * | 1/2014 | Hering | B01D 5/0009 361/226 |
| 2014/0247450 | A1 * | 9/2014 | Han | G01N 15/0211 356/338 |
| 2014/0268476 | A1 * | 9/2014 | Han | G01N 15/0656 361/227 |

OTHER PUBLICATIONS

Kuang, Chongai et al., "Modification of Laminar Flow Ultrafine Condensation Particle Counters for the Enhanced Detection of 1nm Condensation Nuclei," Aerosol Science and Technology, 46:309-315, 2012 (8 pages).

* cited by examiner

METHOD AND SYSTEM FOR SIGNIFICANTLY IMPROVING CHARGE PROBABILITIES OF NANOMETER AEROSOL PARTICLES

CROSS-REFERENCE TO RELATED APPLICATIONS

This application claims the benefit of U.S. Provisional Patent Application No. 61/786,993, filed Mar. 15, 2013 and titled "METHOD AND SYSTEM FOR SIGNIFICANTLY IMPROVING CHARGE PROBABILITIES OF NANOMETER AEROSOL PARTICLES" which application is incorporated herein by reference in its entirety.

FIELD AND BACKGROUND OF THE INVENTION

This invention generally relates to nanoparticle chargers.

Aerosol particles occur in the air we inhale and may have an adverse effect on the human health. In addition, inhalers for medical applications produce different kinds of aerosol particles of different sizes, including nanoparticles where not only the presence but also the size distribution of the aerosol particles is an object of interest. Furthermore, the detection of the aerosol particles and characteristics, such as their generation and the size, is essential in climate study and monitoring exhaust gases along with their particulate matter and implementation of emission standards.

One barrier to the detection of aerosol particles having a diameter in the nanometer range is that they are difficult to be detected optically. A number of techniques exist for detecting aerosol particles having a size smaller than optically detectable, such as first charging the aerosol particle. The charged particles are then collected and the induced electric current is measured in order to detect the presence or the amount of the particles. Also, some detection techniques involve growing the aerosol particles by condensing a certain condensing fluid vapor on the aerosol particles before attempting detection. The most widely used measurement method for submicron aerosol particle size distributions is the electrical mobility-based method, such as through the use of a Scanning Mobility Particle Sizer (SMPS) device. This method and device first charges the aerosol particles to a known charge state with a unipolar or bipolar charger, classifies these charged aerosol particles according to their electrical mobility in an electric field with a differential mobility analyzer (DMA), and then measures aerosol particle concentrations of a specific electrical mobility with a detector. In order to invert the measured electrical mobility data to obtain aerosol particle size distribution, accurate knowledge of aerosol particle charge probability distribution is required. For submicron particles, the Fuchs charge probability model is widely accepted and used.

The electrical mobility-based method works well but it has one key limitation. The main challenge is the low differential mobility analyzer (DMA) throughput because of low charge probabilities of aerosol particles smaller than 100 nm (nanometer). The charge probabilities tend to decrease with decreasing particle size. For instance, the charge probabilities of single charged 22.1 nm and 10.7 nm particles are only about 9% and 4%, respectively. For sub-2.5 nm particles, charge probabilities are almost zero (less than 1%). The low charge probabilities reduce the monodisperse aerosol throughput of a DMA. As a result, the data quality of an SMPS (scanning mobility particle sizer) measurement in this size may be poor because of low counting statistics. The low charge probabilities also mean that a majority of the aerosols are wasted when analyzed with electrical mobility methods. For instance, if the charge probability of a particle of diameter dp is 1%, for this size particle, only 1% of the sample will be analyzed, and 99% of the sample will not be analyzed and get filtered out. Any method to enhance the charge probability of this size particle from 1% to 10%, would generate about 10 times more samples that could be analyzed by the electrical mobility-based method and thus achieve better data quality and less waste of working fluid and sample particles.

Therefore there is a need for improving charge probabilities for submicron nanometer aerosol particles.

SUMMARY

Studies have shown that charge probabilities could be significantly improved by first growing the aerosols to larger sizes before charging them with a charger. This technique, however, to date has very limited use because the resulting aerosol particles contain too many aerosol particle groupings or samples with more than one charge and thus poor monodispersity for DMA-type applications. In other words, the quality of single-size particles is poor and the sample contains too many different size particles. The various embodiments described herein significantly increase charge probabilities of nanoparticles by first growing them to larger droplets in a preconditioner using a working fluid selected from the group including oleic acid, DOS, and diethylene glycol, charging the droplets with a bipolar charger, and then removing the condensed liquid to recover the aerosol nanoparticles. One of the main advantages of our various embodiments desired herein over the prior art is that nanoparticles grow to only about 200 nm, and preferably about 100 nm, compared to a few micrometers size droplets performed in previous studies. The small droplet size is a very important element in reducing the amount of aerosol particles with more than one charge (or conversely desirably increasing the number of singly-charged particles in the sample to be measured or counted). More particles from the nanoparticle sample are usable when they are converted to single-charged particles with the methods described herein. Consequently, the high single-charge particle probability significantly enhances the monodisperse aerosol throughput of a DMA, while the reduced multiple charge probabilities ensure high monodispersity of DMA-classified aerosols and ensure good data quality of SMPS (scanning mobility particle system) measurements.

The various embodiments described herein use generally known techniques for growing the particles in an aerosol but use different working fluids, namely, but not limited to oleic acid, dioctyl sebacate (DOS or DEHS), or diethylene glycol (DEG), to grow the aerosol particles. In this example embodiment, the oleic acid, DOS, and DEG working fluids have the advantage of having the capability to activate and grow aerosol particles as small as 1 nm and the final droplet sizes are expected to be around 200 nm, but preferably 100 nm. The small droplet size significantly reduces the amount of aerosol particles with more than one charge which is important for DMA-type applications. For instance, a charge probability of positively singly charged 5 nm particles is about 1.9%, while charge probabilities for higher charges are negligible. For 100 nm droplets, the probabilities for +1, +2 and +3 charges are 21.3%, 3.2% and 0.2%, respectively. For droplet size of 2000 nm, the +1, +2 and +3 charge probabilities are 10.6%, 10.7%, and 4%, respectively. Therefore, growing the sub-100 nm aerosol particles to 100 nm and 2000 nm droplets not only improves the single-charge probabilities, but for the 100 nm droplet this method is a significant improvement in the art because it provides higher single-charged fraction and it also has much less multiple charged fractions than that of the 2000 nm droplet approach. Hence, the described preconditioner device using oleic acid, DOS and DEG working fluids for a 1 nm condensation particle counter application is used to improve nanoparticle charge probability as taught herein.

In one example embodiment, a system is provided for improving submicron particle charge probabilities that includes a preconditioner device adapted to use a high surface tension and low vapor pressure fluid as a working fluid to grow submicron particles to a droplet size having a diameter of less than about 200 nm. The system also includes a charger device operatively coupled to the preconditioner and configured to charge grown particles. The system further includes a size recovery device operatively coupled to the charger device and configured to remove the working fluid and recover single-charged nanoparticles.

In another example embodiment, a method is provided of charging submicron particles comprising the steps of growing submicron particles from a particle laden flow with a working fluid to a grown droplet size having a diameter sufficiently large to hold a single charge. The method also includes the step of charging the grown submicron particles with a charger and then and drying the charged particles with a size recovery device. The method provides a population of single-charged submicron particles that increases as the grown droplet size decreases before charging.

In yet another example embodiment, a nanoparticle measurement system is provided that includes a nanoparticle charger apparatus configured to receive a nanoparticle laden flow and to grow the particles using a working fluid comprised of a fluid having a high surface tension and a low vapor pressure, the charger apparatus is further configured to charge the grown particles before drying the particles. The system also includes a differential mobility analyzer operatively coupled to the nanoparticle charger apparatus and adapted to receive and separate the charged nanoparticles. The system further includes an aerosol detector device operatively coupled to the mobility analyzer and adapted to conduct particle monitoring.

The various embodiments described herein will now be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DESCRIPTION OF THE PREFERRED EMBODIMENTS

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

The various embodiments of the invention are generally based on the fact that large aerosol particles have higher charge probabilities than smaller ones and hence seek to enhance the charge probabilities of sub-100 nm aerosols while minimizing the amount of aerosols with more than one charge. The high charge probability increases DMA throughput and the low multiple charge probability ensures high quality monodispersity which is important for mono-dispersed aerosol generation applications and SMPS size distribution measurements. Charge probability improvement also tends to decrease for aerosol particles equal to and larger than the final droplet size which is believed to be around 100 nm. Since all particles smaller than 100 nm grow to about the same droplet size regardless of their original size, the improvement on charge probability will increase with decreasing particle size. For instance, the single-charge probabilities of 2 and 5 nm could increase as much as factor of 28 and 11 times respectively while the improvement for 90 nm sized particles will be only 1.02 times. This is not an issue since single-charge probabilities for large particles are already fairly high (about 21% for 90 nm).

Figure 1:
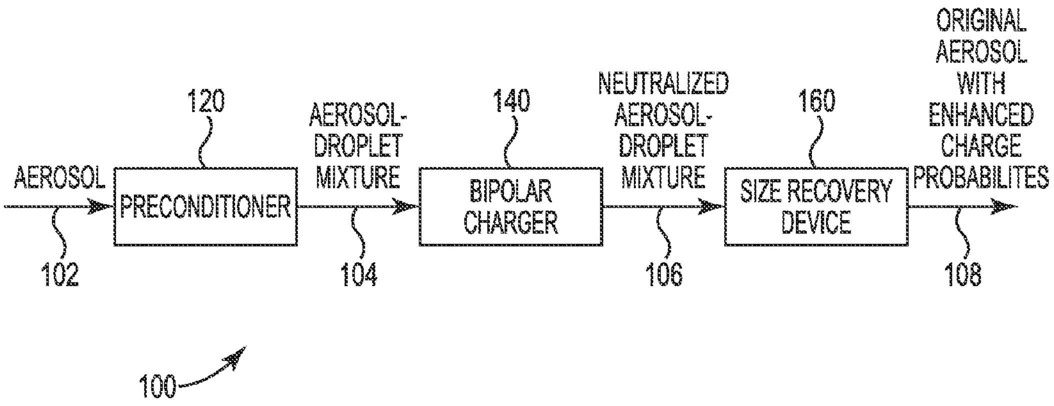
FIG. 1 illustrates a flow diagram and system components for growing, charging and recovering nanoparticles according to the teachings herein.
Figure 2:
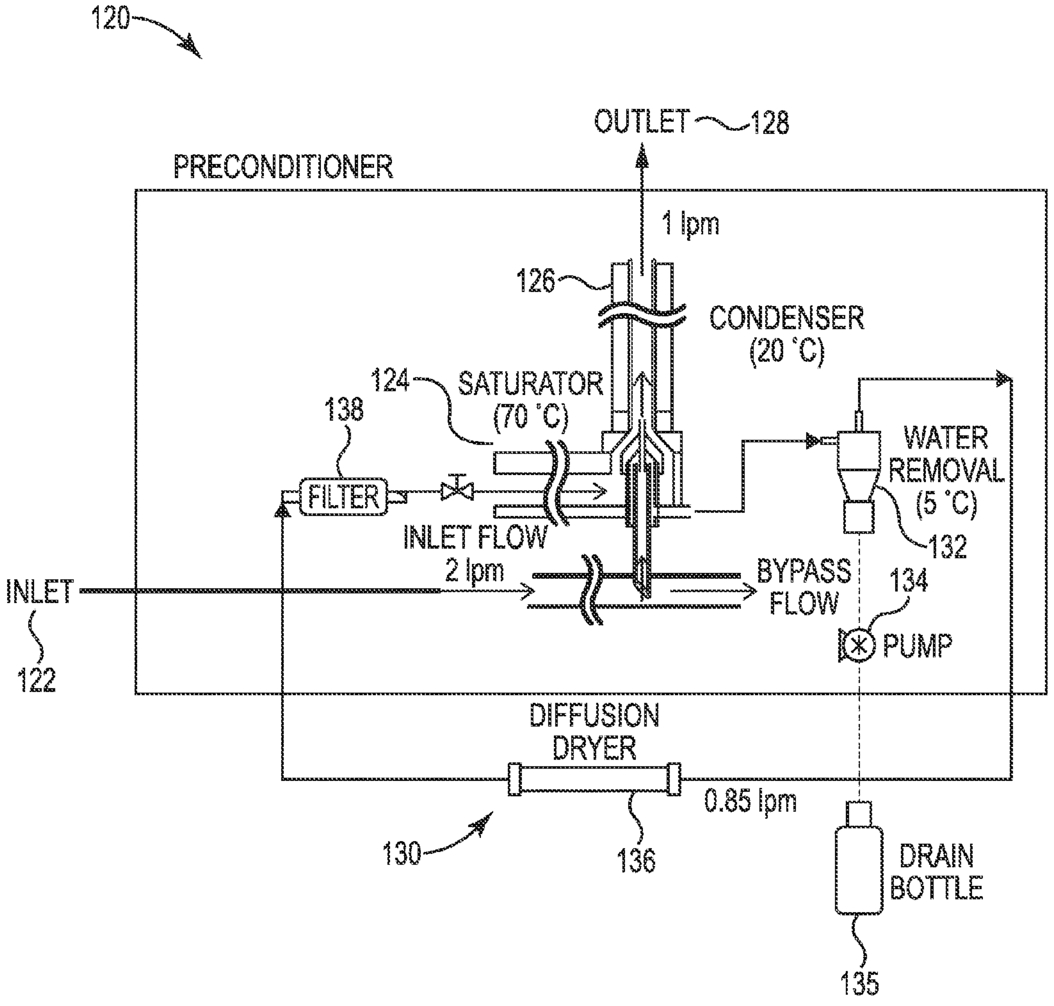
FIG. 2 illustrates a more detailed schematic diagram of a preconditioner for charging nanoparticles as taught herein.

Referring now to FIGS. 1 and 2, in one example embodiment, a nanoparticle charger system 100 for growing (and later counting) sub-100 nm particles in an aerosol includes a preconditioner stage or device 120, a bipolar charger 140 and a size recovery device 160. Particle-laden aerosols 102 are first introduced to a preconditioner 120, which uses well-known condensation particle counter (CPC) thermal diffusive and condensation techniques to grow particles to a certain droplet size. Unlike traditional CPCs which use water, butanol, or isopropanol as the working fluid, preconditioner 120 uses oleic acid, DOS or diethylene glycol (DEG), but is not limited to such as working fluids (see Iida 2009 article referenced herein for more examples of working fluids), which can activate and grow aerosol particles as small as 1 nm. In addition, the droplets grow to only about 100 nm compared to about a few micrometers size droplets typically from traditional CPC methods. Since aerosols smaller than 100 nm will grow to about 100 nm while aerosols larger than 100 nm are likely to grow very little, it is generally assumed that these aerosols retain their original sizes.

Referring again to FIG. 1, a droplet-aerosol mixture 104 is then charged with a bipolar charger 140 (such as Kr-85 neutralizer) to obtain known charge fractions according to the Fuchs charge distribution. Once the nanoparticles are charged as aerosol 106, the next step is to remove the working fluid condensed on the aerosol nanoparticles and to recover the original particles of the aerosols with a size recovery stage or device 160. In this example embodiment, the size recovery technique used within the size recovery stage is comprised of, but not limited to, simply heating the charged aerosol flow 106 sufficiently to evaporate the working fluid so as to recover the original aerosol nanoparticles 108.

Referring again to FIG. 2, there is illustrated in more detail an example embodiment of preconditioner 120 of nanoparticle charger system 100. In particular, preconditioner 120 includes an inlet 122 for a submicron particle laden aerosol 102 having an inlet flow speed of about 2 lpm (liters per minute). Part of aerosol 102 flows through as a bypass flow while another portion of aerosol 102 flows through a saturator body 124 that is laden with a working fluid, such as oleic acid, DOS or diethylene glycol vapor. In this example embodiment, saturator body 124 is kept at about 70° C. but in related embodiments and depending on the type of working fluid used, the temperature range for the saturator body is from about 40° C. to about 80° C. A system 130 provides a filtered air flow (later used as a sheath flow for particle laden flow) and a water collection method to the flow of preconditioner 120, which is comprised of a water removal device 132, a pump 134, a drain bottle 135 that collects excess water moisture in the air. System 130 provides filtered air that flows through saturator body 124, which envelopes (or sheath) particle aerosol flow 102 as it flows through condenser 126. The filtered air flows through a diffusion dryer 136 and a filter 138 that filters the clean air flowing through saturator 124.

The submicron or nanoparticles in aerosol 102 are then grown in condenser stage 126, which in this example embodiment is held to about 20° C., before exiting outlet 128 at a flow of about 1 lpm (emerging as grown submicron or nanoparticles particles 104 as shown in FIG. 1). In related embodiments, the temperature range of the condenser stage is from about 5° C. to about 25° C.

In one example embodiment, a system is provided for improving submicron particle charge probabilities that includes a preconditioner device adapted to use a high surface tension and low vapor pressure fluid as a working fluid to grow submicron particles to a droplet size having a diameter of less than about 200 nm. The system also includes a charger device operatively coupled to the preconditioner and configured to charge grown particles and a size recovery device operatively coupled to the charger device and configured to remove the working fluid and recover single-charged nanoparticles. In one embodiment, the preconditioner device further includes a thermally diffusive condensation particle counter device adapted to grow the submicron particles. In this embodiment, the preconditioner device further includes a saturator device coupled to the condenser. In a related embodiment, the preconditioner device further includes a means for providing a sheath of filtered air about the nanoparticles.

In another example embodiment, a method is provided of charging submicron particles comprising the steps of growing submicron particles from a particle laden flow with a working fluid to a grown droplet size having a diameter sufficiently large to hold a single charge. The method also includes the step of charging the grown submicron particles with a charger and then and drying the charged particles with a size recovery device. The method provides a population of single-charged submicron particles increases as the grown droplet size decreases before charging. In a related embodiment, the method further includes the step of growing the submicron particles includes using a thermally diffusive condensation process with a working fluid that includes diethylene glycol (DEG). In a related embodiment, the method further includes the steps of using a differential mobility analyzer to separate the particles and using a condensation particle counter coupled to the mobility analyzer to monitor the particles. In this example embodiment, the droplet is grown to a size of about less than 200 nm in diameter. In a related embodiment of the method, the droplet is grown to a size of about less than 100 nm in diameter. In a related embodiment, the size recovery device includes one of a diffusion-type dryer or heating element. In this example embodiment, the method further includes the step of providing the nanoparticles in a laminar flow and further includes the step of providing a sheath of filtered air about the nanoparticle flow. In this embodiment, the submicron particles comprise particles of about less than 100 nm in size and the working fluid is comprised of a fluid having a high surface tension and a low vapor pressure. In a related example embodiment, the working fluid is selected from the group consisting of oleic acid, dioctyl sebacate (DOS or DEHS), diethylene glycol (DEG).

In yet another example embodiment, a nanoparticle measurement system is provided that includes a nanoparticle charger apparatus configured to receive a nanoparticle laden flow and to grow the particles using a working fluid comprised of a fluid having a high surface tension and a low vapor pressure, the charger apparatus is further configured to charge the grown particles before drying the particles. The system also includes a differential mobility analyzer operatively coupled to the nanoparticle charger apparatus and adapted to receive and separate the charged nanoparticles. The system further includes an aerosol detector device operatively coupled to the mobility analyzer and adapted to conduct particle monitoring. In a related embodiment, the nanoparticler charger apparatus includes a preconditioner device configured to grow the particles and a bipolar charger configured to charge the grown particles, and a size recovery device configured to dry the particles after they are charged. In a related embodiment, the aerosol detector is selected from the group consisting of a condensation particle counter (CPC) and an aerosol electrometer. In this example embodiment, the high surface tension and low vapor pressure working fluid is selected from the group consisting of oleic acid, dioctyl sebacate (DOS or DEHS), and diethylene glycol (DEG). In an example embodiment, the preconditioner device is configured to generate grown particles having a droplet size with a diameter less than about 200 nm.

The following patents and publications that relate to particle charger and measurement devices are herein incorporated by reference in their entirety and constitute part of the disclosure herein: U.S. Pat. No. 7,407,531; US2012/0131989; *Effect of Working Fluid on Sub*-2 *nm Particle Detection with a Laminar Flow Ultrafine Condensation Particle Counter*; Iida et. Al., Aerosol Science and Technology, 43:81-96, 2009; and *Modification of Laminar Flow Ultrafine Condensation Particle Counters for the Enhanced Detection of* 1 *nm Condensation Nuclei*; Kuang et. Al., Aerosol Science and Technology, 46:309-315, 2012.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

What is claimed is:

1. A nanoparticle measurement system comprising:

a nanoparticle charger apparatus configured to receive a nanoparticle laden laminar flow, the charger apparatus including a preconditioner device having a saturator configured to introduce a working fluid to the nanoparticle laden flow and including a condenser coupled thereto configured to grow the particles using the working fluid comprised of a fluid having a high surface tension and a low vapor pressure so as to increase particle charge probabilities of the nanoparticles and achieve a low multiple charge probability of the particles, wherein a temperature within the saturator is 40° C. to 80° C. and a temperature within the condenser is 5° C. to 25° C., the charger apparatus further configured to charge the grown particles to obtain known charge fractions according to a Fuchs charge distribution before drying the particles to remove the working fluid;

a differential mobility analyzer (DMA) operatively coupled to said nanoparticle charger apparatus and adapted to receive and separate the charged nanoparticles, wherein a higher charge probability increases throughput in the DMA; and an aerosol detector device operatively coupled to the mobility analyzer and adapted to conduct particle monitoring, wherein the low multiple charge probability of the particles improves monodispersity for size distribution measurements.

2. The measurement system of claim 1 wherein the preconditioner device further includes a filtered air flow system provided to the saturator with a water removal device configured to provide through the saturator a sheath flow for the particle laden flow, a bipolar charger configured to charge the grown particles, and a size recovery device configured to dry the particles after they are charged.

3. The measurement system of claim 1, wherein the aerosol detector is selected from the group consisting of a condensation particle counter (CPC) and an aerosol electrometer.

4. The measurement system of claim 1 wherein the high surface tension and low vapor pressure working fluid is selected from the group consisting of oleic acid, dioctyl sebacate (DOS or DEHS), and diethylene glycol (DEG).

5. The measurement system of claim 2 wherein the preconditioner device is configured to generate grown particles having a droplet size with a diameter of 100 nm or less.

6. A system for improving submicron particle charge probabilities comprising:

a preconditioner device adapted to use a high surface tension and low vapor pressure fluid as a working fluid so as to increase submicron particle charge probabilities of nanoparticles and obtain known charge fractions and to grow submicron particles in a particle laden laminar flow to a droplet size having a diameter of less than 200 nm, the preconditioner device having a saturator configured to introduce the working fluid to the nanoparticle laden flow and including a condenser coupled thereto configured to grow the particles using the working fluid, wherein a temperature within the saturator is 70° C. and a temperature within the condenser is 20° C.;

a charger device operatively coupled to said preconditioner device and configured to charge the grown nanoparticles; and a size recovery device operatively coupled to said charger device and configured to remove the working fluid and recover single-charged nanoparticles due to a low multiple charge probability of the particles.

7. The system of claim 6 wherein the preconditioner device further comprises a thermally diffusive condensation particle counter device adapted to grow the submicron particles.

8. The system of claim 6 wherein the preconditioner device further comprises a filtered air flow system with a water removal device configured to provide through the saturator a sheath of filtered air about the particle laden flow of nanoparticles.

9. A method of charging submicron particles comprising the steps of:

growing submicron particles with a condenser from a particle laden laminar flow with a high surface tension and a low vapor pressure working fluid provided by a saturator so as to increase submicron particle charge probabilities and obtain known charge fractions, the submicron particles being grown to a droplet size having a diameter sufficiently large to hold a single charge, wherein a temperature within the saturator is 40° C. to 80° C. and a temperature within the condenser is about 5° C. to 25° C., wherein a population of single-charged submicron particles increases as the grown droplet size decreases before charging;

charging the grown submicron particles with a charger; and drying the charged particles with a size recovery device.

10. The method of claim 9 wherein the step of growing the submicron particles includes using a thermally diffusive condensation process with a working fluid that includes oleic acid, dioctyl sebacate (DOS or DEHS) or diethylene glycol (DEG).

11. The method of claim 9 further including the steps of using a differential mobility analyzer, after drying the charged grown particles, to separate the single charge particles and using a condensation particle counter coupled to the mobility analyzer to monitor the particles.

12. The method of claim 9 wherein the droplet is grown to a size of 200 nm or less in diameter.

13. The method of claim 10 wherein the droplet is grown to a size of 100 nm or less in diameter.

14. The method of claim 9 wherein the size recovery device includes one of a diffusion-type dryer or heating element.

15. The method of claim 9 further comprising the step of providing a filtered air flow with water removed therefrom through the saturator thereby providing a sheath of filtered air about the nanoparticle laminar flow flowing through the condenser as the submicron particles are grown before being charged.

16. The method of claim 9 wherein the submicron particles comprise particles of less than 100 nm in size.

* * * * *